(12) United States Patent
Karpman et al.

(10) Patent No.: US 10,265,516 B2
(45) Date of Patent: Apr. 23, 2019

(54) CLOSELY SPACED ARRAY OF PENETRATING ELECTRODES

(71) Applicant: The Charles Stark Draper Laboratory, Inc., Cambridge, MA (US)

(72) Inventors: Maurice S. Karpman, Brookline, MA (US); Andrew Meuller, Somerville, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 53 days.

(21) Appl. No.: 15/357,500

(22) Filed: Nov. 21, 2016

(65) Prior Publication Data

US 2017/0165474 A1   Jun. 15, 2017

Related U.S. Application Data

(60) Provisional application No. 62/265,697, filed on Dec. 10, 2015.

(51) Int. Cl.
| | |
|---|---|
| *A61N 1/05* | (2006.01) |
| *H05K 1/02* | (2006.01) |
| *A61B 5/00* | (2006.01) |
| *H05K 3/00* | (2006.01) |
| *A61N 1/36* | (2006.01) |

(Continued)

(52) U.S. Cl.
CPC ........ *A61N 1/0502* (2013.01); *A61B 5/04001* (2013.01); *A61B 5/685* (2013.01); *A61N 1/0551* (2013.01); *A61N 1/36139* (2013.01); *H05K 1/028* (2013.01); *H05K 1/09* (2013.01); *H05K 1/111* (2013.01); *H05K 3/0026* (2013.01); *H05K 3/40* (2013.01); *H05K 3/4644* (2013.01); *H05K 3/4682* (2013.01); *A61B 2562/043* (2013.01); *A61B 2562/125* (2013.01);

(Continued)

(58) Field of Classification Search
CPC .............. A61N 1/0476; A61N 1/37205; A61N 1/0502; A61N 1/0551; A61N 1/36139; A61B 5/685; A61B 5/04001; A61B 2562/043; A61B 2562/125; H05K 1/028; H05K 3/0026; H05K 1/09; H05K 1/111; H05K 3/40; H05K 3/4644; H05K 3/4682; H05K 2203/107; H05K 2201/05; H05K 2201/09372

See application file for complete search history.

(56) References Cited

U.S. PATENT DOCUMENTS

| | | | |
|---|---|---|---|
| 2007/0096281 A1 | 5/2007 | Greenberg et al. | |
| 2009/0177144 A1* | 7/2009 | Masmanidis | ...... A61B 5/04001 604/66 |

(Continued)

OTHER PUBLICATIONS

International Search Report and Written Opinion dated Feb. 13, 2017 in PCT Application No. PCT/US2016/063102.

*Primary Examiner* — Catherine M Voorhees
(74) *Attorney, Agent, or Firm* — McDermott Will & Emerry LLP

(57) ABSTRACT

The present disclosure describes a closely spaced array of penetrating electrodes. In some implementations, the electrodes of the array are spaced less than 50 μm apart. The present disclosure also describes methods for manufacturing the closely spaced array of penetrating electrodes. In some implementations, each row of electrode of the array is manufactured in-plane and then coupled to other rows of electrodes to form an array.

15 Claims, 11 Drawing Sheets

(51) Int. Cl.
 *A61B 5/04* (2006.01)
 *H05K 1/11* (2006.01)
 *H05K 3/40* (2006.01)
 *H05K 3/46* (2006.01)
 *H05K 1/09* (2006.01)
(52) U.S. Cl.
 CPC ............... *H05K 2201/05* (2013.01); *H05K 2201/09372* (2013.01); *H05K 2203/107* (2013.01)

(56) References Cited

U.S. PATENT DOCUMENTS

2012/0287420 A1* 11/2012 McLaughlin ........ A61B 5/0084
 356/72
2014/0046417 A1 2/2014 Schuettler et al.
2015/0335258 A1* 11/2015 Masmanidis ........ A61B 5/6868
 600/378

* cited by examiner

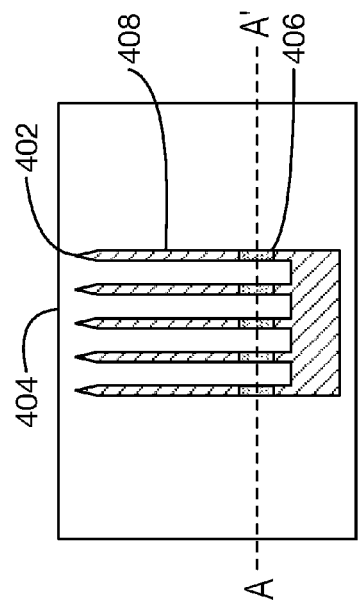
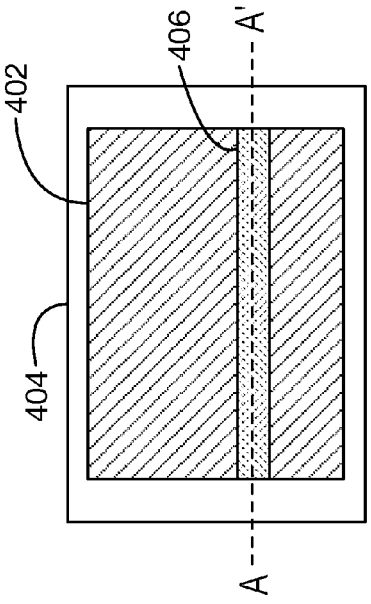
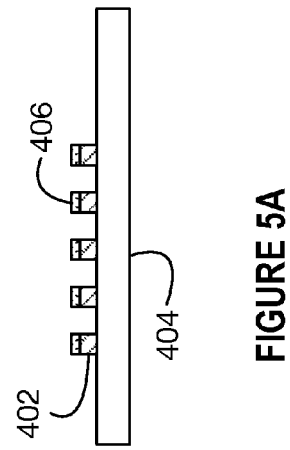
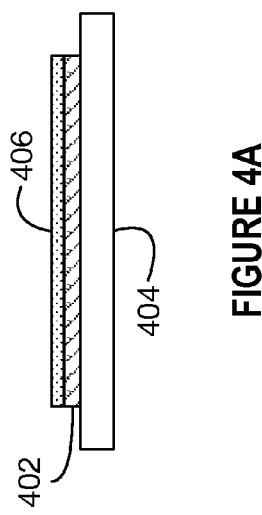
FIGURE 4B
FIGURE 5B
FIGURE 4A
FIGURE 5A

CLOSELY SPACED ARRAY OF PENETRATING ELECTRODES

RELATED APPLICATIONS

This application claims priority to U.S. Provisional Patent Application No. 62/265,697, titled "CLOSELY SPACED ARRAY OF PENETRATING ELECTRODES" and filed Dec. 10, 2015, the entire contents of which are incorporated herein by reference.

BACKGROUND OF THE DISCLOSURE

Electrodes can be implanted into target tissue to record from and stimulate the target tissue. For example, depth electrodes can be implanted into peripheral nerves or brain tissue. The electrical signals recorded by the electrode can aid in the diagnosis and treatment of neurological diseases.

SUMMARY OF THE DISCLOSURE

According to one aspect of the disclosure, an electrode array includes a plurality of electrode shanks. Each of the shanks includes a conductive core defined in a first metal layer. The shanks have a pitch between about 10 μm and about 50 μm. The electrode array also includes an insulative layer encapsulating at least a portion of the first metal layer. An electrode is defined in each of the plurality of electrode shanks by a first window defined through the insulative layer. A contact pad is defined in each of the plurality of electrode shanks by a second window defined though the insulative layer. The electrode array also includes a carrier substrate. The plurality of electrode shanks are coupled to a surface of the carrier substrate such that the plurality of electrode shanks extend outward from and parallel to the carrier substrate.

In some implementations, the electrode array also includes a second plurality of electrode shanks coupled to the first plurality of electrode shanks. Each of the second plurality of electrode shanks can include an offset wherein a contact pad is defined in each of the second plurality of electrode shanks.

In some implementations, each of the plurality of electrode shanks are between about 5 μm and about 100 μm wide or between about 5 μm and about 15 μm wide. In some implementations, the electrode array includes between about 2 and about 32 electrode shanks.

In some implementations, each of the electrodes defined in each of the plurality of electrode shanks are defined a different distance from a tip of their respective electrode shank. At least a portion of the carrier substrate is flexible in some implementations. The certain implementations, the first metal layer includes a platinum iridium foil. The foil can be between about 10 μm and about 40 μm thick. In some implementations, each of the plurality of electrode shanks includes a copper core. In some implementations, the contact pad of each of the plurality of electrode shanks is electrically coupled to a trace of the carrier substrate by wire bonding.

According to another aspect of the disclosure, a method of manufacturing an electrode includes forming a first plurality of electrode shanks in a first metal layer. A pitch between each of the plurality of electrode shanks is between about 10 μm and about 50 μm. The method also includes encapsulating at least a portion of each of the first plurality of electrode shanks in an insulating material. A window is defined through the insulating material encapsulating each of the first plurality of electrode shanks. The method also include coupling the first plurality of electrode shanks to a carrier substrate, such that the plurality of electrode shanks extend outward from and parallel to the carrier substrate to which plurality of electrode shanks are coupled.

In some implementations, the method also includes depositing a gold layer on at least a portion of the first metal layer prior to encapsulating the portion of the plurality of electrode shanks.

The method can also include defining a second window through the insulating material encapsulating each of the first plurality of electrode shanks above the deposited gold layer. In some implementations, the windows are defined by laser ablating the insulating material.

In some implementations, the method includes wire bonding each of the first plurality of the electrode shanks to an electrical trace of the carrier substrate. In some implementations, the first metal layer includes a platinum iridium foil.

In some implementations, the method includes singulating each of the first plurality of electrode shanks after coupling the first plurality of electrode shanks to a carrier substrate.

In some implementations, the method also includes releasing the patterned first plurality of electrode shanks from a first release layer, and coupling the patterned first plurality of electrode shanks to a second release layer, wherein a portion of each of the patterned first plurality of electrode shanks extend over an edge of the second release layer.

In some implementations, the method also includes depositing a copper layer on a portion of the first metal layer and encapsulating the copper layer with a second metal layer. In some implementations, the insulating material is deposited on the portion of the plurality of electrode shanks with chemical vapor deposition.

According to another aspect of the disclosure, a method of manufacturing an electrode includes depositing a first metal layer on a sacrificial layer. The first metal layer defines a face of a first plurality of electrode shanks. A pitch between each of the plurality of electrode shanks is between about 10 μm and about 50 μm. The method also includes depositing a first sacrificial metal layer on at least a portion of the first metal layer and the sacrificial layer, and then planarizing the first sacrificial metal layer and the first metal layer to form a first layer. The method also includes depositing a second metal layer on the first layer. The second metal layer defines walls of each of the first plurality of electrode shanks. Then a second sacrificial metal layer is deposited on at least a portion of the second metal layer and first layer. The second sacrificial metal layer and the second metal layer are planarized to form a second layer. The method also includes depositing a third metal layer on the second layer. The third metal layer defines a second face of each of the first plurality of electrode shanks. Next, a third sacrificial metal layer is deposited on at least a portion of the third metal layer and second layer. The third sacrificial metal layer and the third metal layer are planarized to form a third layer. Finally, at least a portion of the first, second, and third sacrificial metal layers are dissolved.

In some implementations, the first, second, and third sacrificial metal layers include copper and the first, second, and third metal layers include palladium.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 4A-12 illustrate a series of cross-sectional and top views at different steps of manufacturing an example penetrating electrode array using the method illustrated in FIG. 3.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
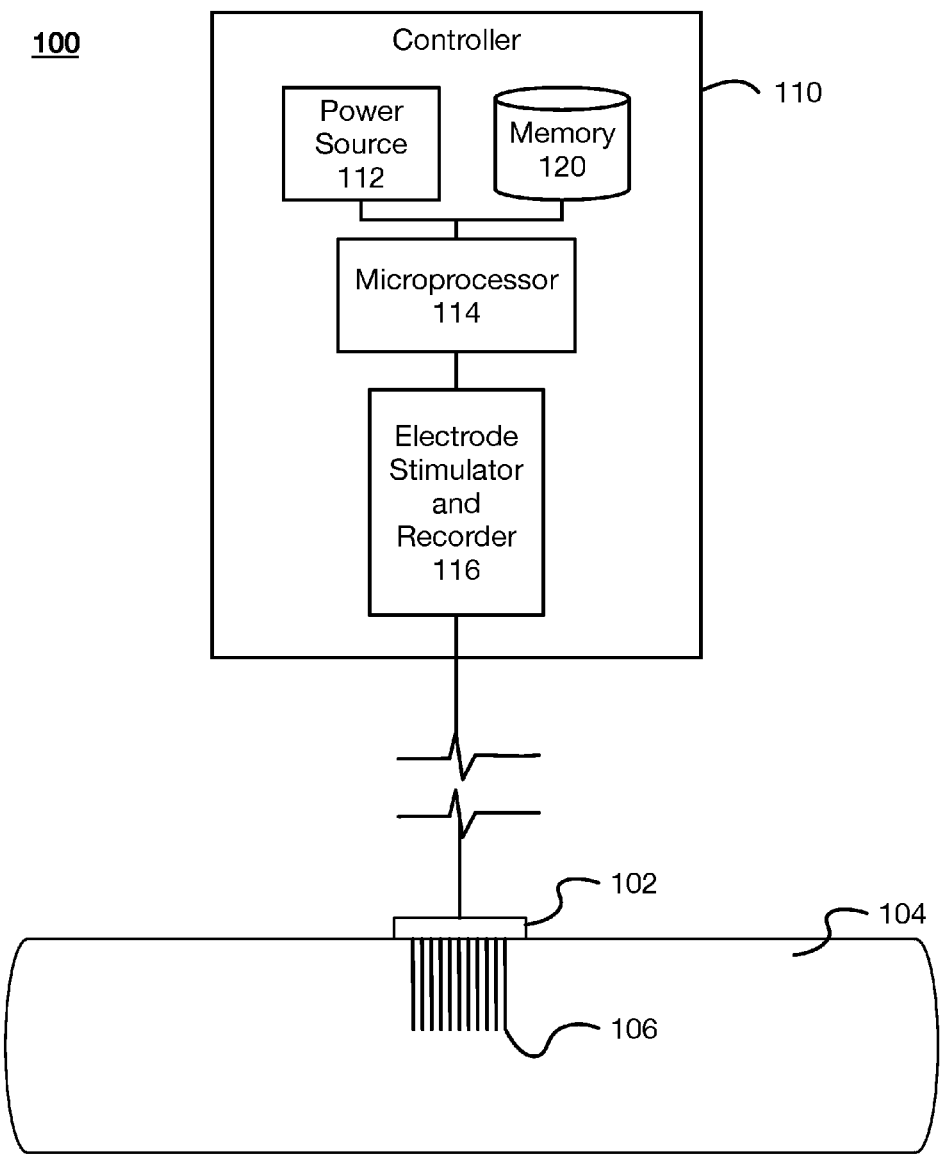
FIG. 1 illustrates an example system for stimulating and monitoring tissue with an example penetrating electrode array.

FIG. 1 illustrates an example system 100 for stimulating and monitoring tissue with an example penetrating electrode array 102. The system 100 includes a penetrating electrode array 102 inserted into a nerve 104, which is also referred to as a target tissue 104. The electrode array 102 includes a plurality of electrode shanks 106 that penetrate into the nerve 104. The electrode array 102 is coupled to and controlled by a controller 110. The controller 110 is powered by a power source 112 and includes a microprocessor 114 that controls an electrode stimulator and recorder (ESR 116). The data recorded by the ESR 116 can be stored in memory 120 for later transfer and analysis.

The controller 110 of the system 100 controls the stimulation and monitoring of the tissue 104 via the electrode array 102. In some implementations, the controller 110 is a hermetically sealed device that is configured for chronic implantation near the target tissue 104. In other implementations, the controller 110 is a handheld device or computer that resides outside of the patient and communicates wirelessly or via a wired connection to the electrode array 102. The controller 110 includes one or more microprocessors 114 that control the function of the ESR 116. The microprocessor 114 can be any type of single or multi-core processor or special purpose logic circuitry such as an FPGA (field programmable gate array) or an ASIC (application specific integrated circuit). In some implementations, the controller 110 outputs data to other devices for analysis. The controller 110 can communicate with the other devices wirelessly or through a wired connection.

The ESR 116 of the controller 110 generates electrical stimuli that are used to stimulate the tissue 104 via electrodes disposed along each of the plurality of electrode shanks 106. For example, the ESR 116 can generate electrical pulses or waves, and can control the frequency, pulse width, signal shape (e.g., square vs. sinusoidal shaped), amplitude, or additional properties of the stimulation, such as selecting which electrodes act as stimulating electrodes and which electrodes act as recording electrodes. The ESR 116 can generate a stimulation signal with a frequency between about 10 Hz and about 25 kHz, between about 10 Hz and about 10 kHz, between about 100 Hz and about 1 kHz, or between about 100 Hz and about 500 Hz. The ESR 116 also includes one or more analog to digital converters (ADC) that converts the measured electrical activity from the tissue 104 into a digital signal that can be stored in memory 120. The ADCs of the ESR 116 can sample a signal measured at the electrodes disposed along the plurality of electrode shanks 106 at a frequency between about 10 Hz and about 10 kHz, between about 10 Hz and about 5 kHz, between about 10 Hz and about 1 kHz, between about 50 Hz and about 500 Hz, or between about 50 Hz and about 250 Hz.

The controller 110 of the system 100 also includes a power source 112. When the controller 110 is implanted into a patient, the power source 112 is a battery. In implementations where the controller 110 is external the to the patient, the power source 112 can be a battery or the controller 110 may be plugged into an AC power source (e.g., a wall outlet). In some implementations, the battery of the power source 112 is rechargeable. For example, the controller 110 can include a plurality of induction coils that enable the battery to be wirelessly recharged after the controller 110 is implanted into the patient.

Still referring to FIG. 1, the system 100 also includes an electrode array 102. The electrode array 102 is described further in relation to FIGS. 2-14G, but as an overview the electrode array 102 includes a plurality of electrode shanks 106. Electrodes are disposed along each of the electrode shanks 106. In some implementations, the electrode array 102 includes a single row of aligned electrode shanks 106. In other implementations, the electrode array 102 includes multiple rows of aligned electrode shanks 106 to form a three-dimensional electrode array. In some implementations, the pitch between electrode shanks 106 is less than 50 μm. In some implementations, the rows of the electrode shanks 106 are manufactured "in plane" and then stacked upon one another to form a three-dimensional electrode array. In some implementations, the small pitch size (e.g., pitches less than 50 μm) enables recording and stimulation in peripheral nerves. In many instances, peripheral nerves have a diameter less than 100 μm. Additionally, the peripheral nerves often include bundles of axons within the body of the nerve. The small pitch size enables not only multiple electrode to be inserted into the nerve, but electrodes to be placed in each of the bundles of axons within the nerve.

Figure 2:
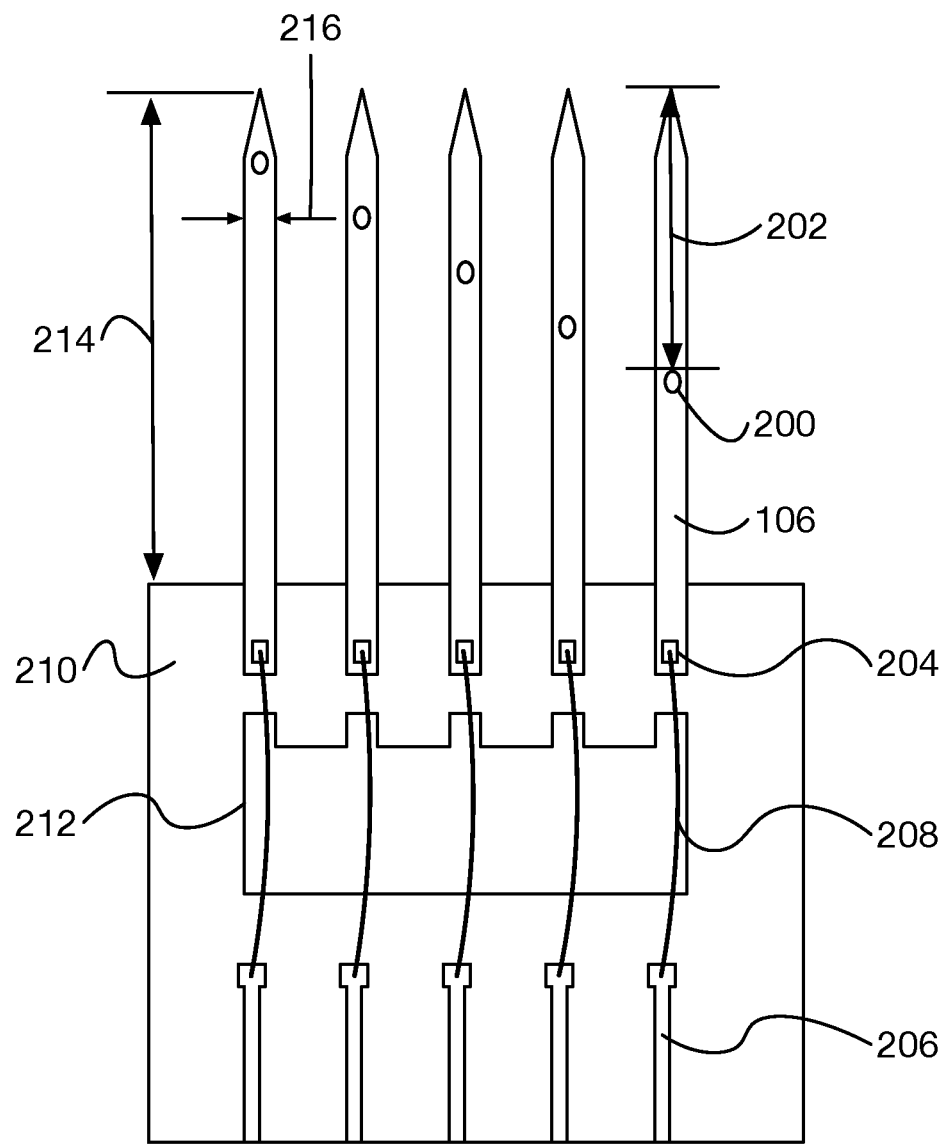
FIG. 2 illustrates an example penetrating electrode array for use in the system illustrated in FIG. 1.

FIG. 2 illustrates an example electrode array 102 for use in the system 100. The electrode array 102 includes electrode shanks 106. Each of the electrode shanks 106 includes an electrode 200 a predetermined distance 202 from a tip of the electrode shanks 106. The base of each of the electrode shanks 106 includes a contact pad 204. The electrode shanks 106 are coupled to a carrier substrate 210. Each of the electrode shanks 106 is coupled to a trace 206 of the carrier substrate 210 by a wire 208 that wire bonds the contact pad 204 to the trace 206. In some implementations, during the manufacturing process each of the electrode shanks 106 is coupled to a common base 212. Once the common base 212 and electrode shanks 106 are coupled to the carrier substrate 210, the electrode shanks 106 are singulated by ablating a portion of each of the electrode shanks 106 that connects the electrode shanks 106 to the common base 212. As illustrated in FIG. 2, the common base 212 can remain coupled to the carrier substrate 210 after separation from the electrode shanks 106.

The electrode array 102 includes a plurality of electrode shanks 106. As illustrated the electrode array 102 includes a row of five electrode shanks 106. In other implementations, each row of electrode shanks 106 can include between about 2 and about 128, between about 2 and 64, between about 2 and 32, or between about 8 and about 16 shanks 106. The length 214 of each of the electrode shanks 106, as measured from the end of the carrier substrate 210 to the tip of the electrode shank 106, is between about 50 µm and about 2000 µm, between about 250 µm and about 2000 µm, between about 500 µm and about 2000 µm, between about 1000 µm and about 2000 µm, or between about 1500 µm and about 2000 µm long.

The width 216 of each of the electrode shanks 106 is between about 5 µm and about 100 µm, between about 20 µm and about 80 µm, or between about 40 µm and 60 µm wide. In some implementations, the thickness of each of the electrode shanks 106 is between about 5 µm and about 50 µm, between about 10 µm and about 40 µm, or between about 15 µm and about 30 µm thick. As illustrated, each of the electrode shanks 106 includes a pointed tip. In other implementations, the tip can include a blunt or rounded configuration.

In some implementations, the pitch between each of the electrode shanks is between about 10 µm and about 500 µm, between about 10 µm and about 400 µm, between about 10 µm and about 300 µm, between about 10 µm and about 200 µm, between about 10 µm and about 100 µm, between about 10 µm and about 50 µm, or between about 10 µm and about 25 µm. In some implementations, when the electrode array 102 includes multiple rows of electrode shanks 106, the pitch of the multiple rows of electrode shanks 106 is similar to the pitch of the electrode shanks 106 within each row. In other implementations, the pitch between rows of electrode shanks 106 is greater than or less than the pitch between the electrode shanks 106 within each row.

In some implementations, one or more of the electrode shanks 106 have a different width, thickness, or length when compared to the other electrode shanks 106 of the electrode array 102. For example, the central electrode shank 106 may be the longest, with the two electrode shanks 106 next to the central electrode shank 106 being slightly shorter, and the outside two electrode shanks 106 being the shortest. In some implementations, the electrode shanks 106 can include different tip configurations. For example, a longest electrode shank 106 can include a pointed tip and the other electrode shanks 106 can include blunt tips.

Each of the electrode shanks 106 of the electrode array 102 includes at least one electrode 200. In some implementations, the electrode shank 106 includes a conductive core—for example, the electrode shank 106 can include a platinum iridium core. The core of the electrode shank 106 is encapsulated with an insulating material. In some implementations, the electrode 200 is defined by a window through the insulating material that exposes the core of the electrode shank 106 to the environment. The window defining the electrode 200 can be circular, rectangular, or can include a band that wraps around the circumference of the electrode shank 106. In some implementations, the insulating material is removed from the tip of the electrode shank 106 to define an electrode at the tip of the electrode shank 106.

Each of the electrodes 200 is a predetermined distance 202 from the tip of its electrode shank 106. In some implementations, as illustrated in FIG. 2, the distance 202 is different for each of the electrode shanks 106. In other implementations, the distance 202 between the electrode 200 and the tip of its electrode shank 106 is the same distance for each electrode shank 106.

The base of each of the electrode shanks 106 includes a contact pad 204. The contact pad 204 is in electrical communication with the electrode 200 through the conductive core of the electrode shank 106. The contact pad 204 is defined by a window through the insulating material of the electrode shank 106 that exposes the conductive core of the electrode shank 106. In some implementations, the area of the conductive core that is exposed to form the contact pad 204 is coated with a metal to enable wire bonding to the contact pad 204. For example, a layer of gold may be sputtered onto the area of the conductive core that becomes the contact pad 204.

The carrier substrate 210 of electrode array 102 enables an electrical connection to each of the electrode shanks 106 (and the electrodes 200 defined thereon) and also provides support for the electrode shanks 106. In some implementations, the carrier substrate 210 is a silicon-based or polyimide-based carrier substrate. The carrier substrate 210 can be a mechanically rigid layer For example, the carrier substrate 210 can be mechanically rigid enough to be metalized and to withstand wire bonding and, in some implementations, solder reflow processing. For example, the carrier substrate 210 can include Kapton™, made available by E. I. du Pont de Nemours and Company; a silicon substrate covered by a polyimide; a metalized alumina or other ceramic; silicon coated with high temperature dielectrics, such as silicon dioxide; benzocyclobutene (BCB); Intervia™, made available by Dow Chemical, multi-layer co-fired ceramic, or printed circuit laminate materials, such as glass fiber reinforced epoxy or Bismaleimide-Triazine (BT) resin). In some implementations, the carrier substrate 210 is rigid and in other implementations the carrier substrate 210 is flexible. The carrier substrate 210 includes a plurality of traces 206. Each trace 206 of the carrier substrate 210 is wire bonded to a contact pad 204 of an electrode shank 106. The end of the traces 206 opposite the end that wire bonds to the contact pad 204 can terminate at a connector to enable the electrode array 102 to be electrically coupled to the controller 110. For example, the traces can terminate in, for example, a Nano Series Connector™, made available by an Omnetics Connector Corporation, Minneapolis Minn.

Figure 3:
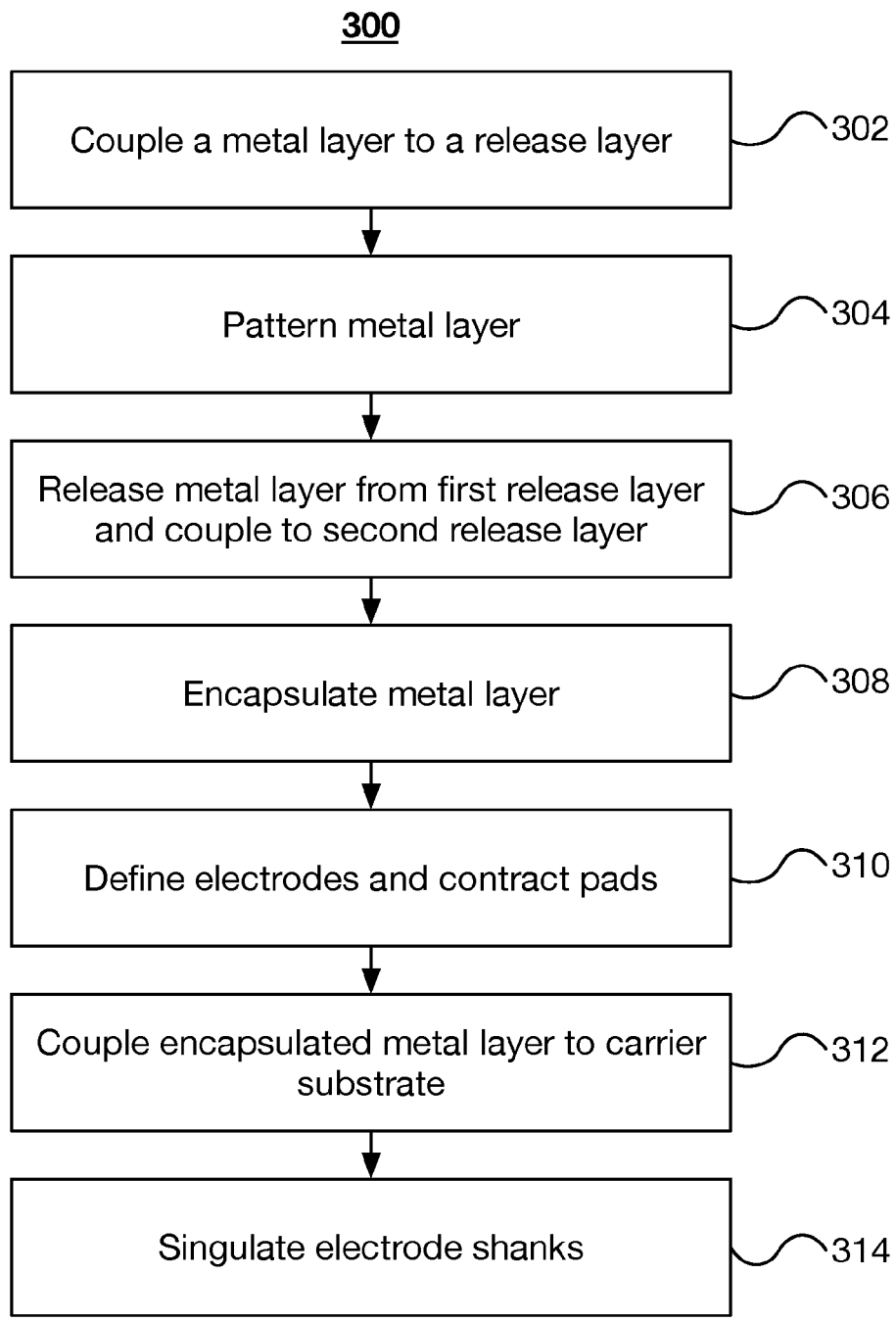
FIG. 3 illustrates a flow chart of an example method for manufacturing an example penetrating electrode array for use with the system illustrated in FIG. 1.

FIG. 3 illustrates a flow chart of an example method 300 for manufacturing an electrode array. For example, the method 300 may be used to manufacture the electrode array 102 illustrated above in relation to FIGS. 1 and 2. The method 300 includes coupling a metal layer to a release layer (step 302). The metal layer is patterned to form a plurality of electrode shanks (step 304). The patterned metal layer is released from a first release layer and coupled to a second release layer (step 306). The metal layer is then encapsulated in an insulating material (step 308). Windows defining electrodes and contact pads are defined through the insulative layer (step 310). The encapsulated metal layer is released from the second release layer and coupled to a carrier substrate (step 312). Each of the electrode shanks are singulated (step 314).

FIGS. 4A-10D illustrate a series of cross-sectional and top views at different steps of manufacturing an electrode array according to the method 300. The cross-sectional views illustrated in FIGS. 4A, 5A, 6A, and 7A are made along the line A-A' in FIGS. 4B, 5B, 6B, and 7B, respectively. In FIGS. 4A-10D, like reference numerals refer to like elements.

Referring to FIGS. 2, 3, 4A, and 4B, the method 300 of manufacturing an electrode array 102 includes coupling a metal layer to a release layer (step 302). As illustrated in FIGS. 4A and 4B, a metal layer metal layer 402 is coupled to a release layer 404. A second metal layer 406 is deposited on at least a portion of the first metal layer 402.

In some implementations, the first metal layer 402 is a foil that is coupled to the release layer 404. The foil can include platinum iridium, gold, palladium, and other electrically conductive, bio-compatible metals. In some implementations, the foil has a thickness of between about 2 μm and about 50 μm, between about 10 μm and about 40 μm, or between about 20 μm and about 30 μm thick. In some implementations, the thickness of the foil is selected such that the foil has sufficient structural rigidity to not substantially deform when inserted into a target tissue.

The release layer 404 is a sacrificial layer that enables the metal layer 402 to be decoupled from an underlying substrate. In some implementations, the release layer 404 is a thermal release tape or an ultraviolet release tape. When the tape is heated or exposed to ultraviolet light, depending on the type of release layer used, a foaming agent within the tape activates and expands to release the metal layer from an underlying substrate. In some implementations, the release layer is a sacrificial material that includes polyimide, polyamide, fluoropolymer, benzocyclobutene, polyphenylquinoxylene, parylene, polynorbornene, polyvinyl acetate, or polyvinyl ethylene which is dissolved or ablated to release the metal layer 402 from an underlying substrate.

In some implementations, a second metal layer 406 is deposited onto the first metal layer 402. In some implementations, the second metal layer 406 is only deposited across a portion of the first metal layer 402. For example, as illustrated in FIG. 4B, the second metal layer 406 is deposited as a band across a portion of the first metal layer 402. In some implementations, a portion of the second metal layer 406 forms the contact pads 204. Accordingly, the material of the second metal layer 406 may be selected to be compatible with wire bonding procedures—for example, the second metal layer 406 can include gold. The layer of gold (or other metals of the second metal layer 406) may be sputtered onto the first metal layer 302 to a thickness of between about 100 angstroms and about 500 angstroms, between about 200 angstroms and 400 angstroms, or between about 200 angstroms and about 300 angstroms thick. In some implementations, a mask is used to limit where the second metal layer 406 is deposited.

Referring to FIGS. 2, 3, 5A, and 5B, the method 300 includes patterning the metal layer 402 (or metal layers 402 and 406) to form a plurality of electrode shanks (step 304). As illustrated, the metal layer 402 and 406 are patterned to define five electrode shanks 408. In some implementations, between about 2 and about 128, between about 2 and 64, between about 2 and 32, or between about 8 and about 16 shanks 408 are patterned into the metal layer. In some implementations, the metal layers 402 and 406 are laser ablated, or are chemical or plasma etched to form the electrode shanks. As described above, the patterned metal layers form the conductive core of the electrode shanks 106 described above in relation to FIG. 2.

Referring to FIG. 3, the method 300 also includes releasing the patterned metal layers from the release layer and coupling the patterned metal layer to a second release layer (step 306). As described above the release layer is configured to release the metal layer from the underlying substrate when exposed to a release agent—for example, a predetermined temperature, ultraviolet light, or a chemical. Accordingly, to release the patterned metal layers from the first release layer 404, the first release layer 404 is exposed to the release agent. Once released from the first release layer 404, the patterned metal layers are coupled to a second release layer.

When coupled to the second release layer, at least a portion of the electrode shanks 408 are positioned to extend beyond an end of the second release layer. For example, a portion of each of the electrode shanks 408 overhangs the second release layer such the underside of the electrode shanks 408 can be coated with an insulating material.

Figure 6A:
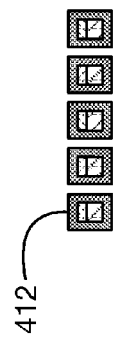
Figure 6B:
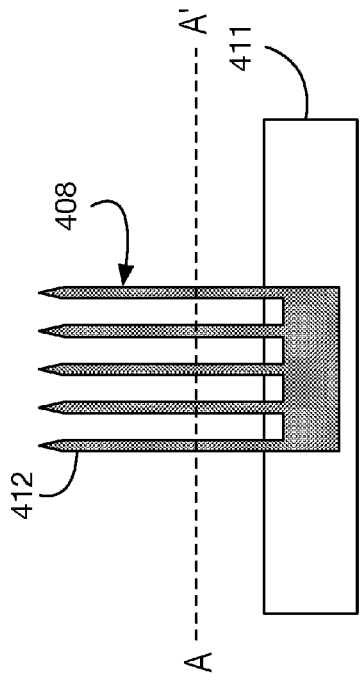

Referring to FIGS. 3, 6A, and 6B, the method 300 includes encapsulating the metal layers with an insulating material (step 308). As illustrated, a portion of each of the electrode shanks 408 extends over an end of the second release layer 411. An insulating material 412 is deposited on the metal layers 402 and 406. FIG. 6B illustrates that the portion of the electrode shanks 408 extending over the second release layer 410 is not supported, which enables an insulative layer to be simultaneously deposited on each face of the electrode shanks 408. In some implementations, the insulating material 412 is a conformal coating applied through vapor deposition. The insulating material 412 can be a biocompatible insulator that can be deposited as a pin-hole free film at temperatures that are compatible with the other components of the electrode array. In some implementations, the insulating material 412 is parylene C (or other vapor deposited fluoropolymers), silicones, or ceramic materials such as alumina or silicon dioxide deposited through a low temperature chemical vapor deposition (CVD), physical vapor deposition (PVD), atomic layer deposition (ALD), or a sol-gel process. In some implementations, the insulating material 412 is applied to be between about 1 μm and about 10 μm, between about 2 μm and about 8 μm, or between about 4 μm and about 6 μm thick.

Figure 7A:
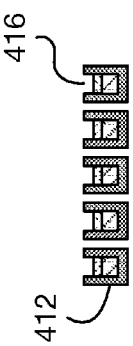
Figure 7B:
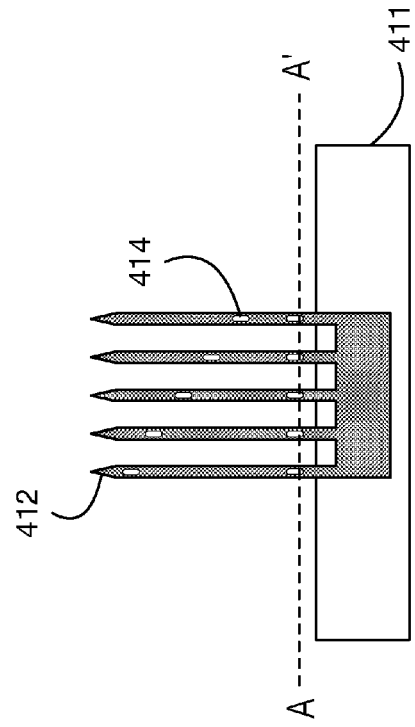

Referring to FIGS. 3, 7A, and 7B, the method 300 includes defining electrodes and contact pads are through the insulative layer (step 310). The electrodes 414 and the contact pads 416 are defined by removing a portion of the insulating material 412 to expose the metal layer below the insulating material 412. For example, the insulating material 412 can be laser ablated with a YAG laser to expose the metal layer 402 or 406. The laser is configured to have a wavelength that ablates the insulative layer 412 without damaging the metal layer 402 or 406 below.

Figure 8:
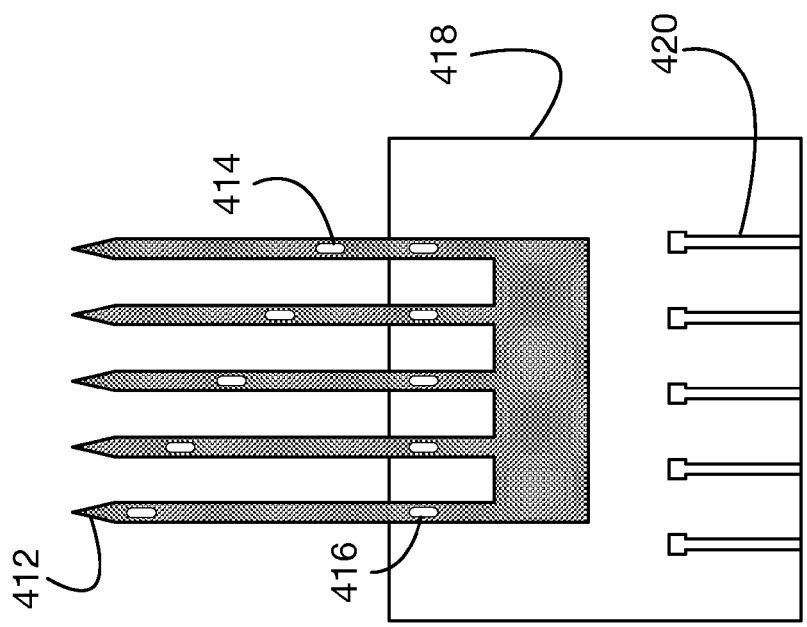

Referring to FIGS. 2, 3 and 8, the method also includes releasing the encapsulated metal layer from the second release layer and coupling the encapsulated metal layer to a carrier substrate (step 312). FIG. 8 illustrates the encapsulated metal layer coupled to a carrier substrate 418. The encapsulated metal layer is coupled parallel to a primary surface of the carrier substrate 418 such that a portion of each of the electrode shanks 408 extends past the end of the carrier substrate 418. The carrier substrate 418 is similar to the carrier substrate 210 described in relation to FIG. 2. The encapsulated metal layer is coupled to the carrier substrate 418 with an adhesive, such as an epoxy with a glass transition temperature high enough to withstand wire bonding and reflow (e.g., above 100° C.). In some implementations, the insulator coating the shanks is ablated to expose the shank's metal layer to provide a compatible surface for the adhesive to bond. In some implementations, the shanks are bonded using a solder or metal eutectic such as Au/Sn.

The carrier substrate 418 includes a number of traces 420 to couple each of the electrodes 414 to a connector on the carrier substrate 418. In some implementations, the carrier substrate 418 includes one trace 420 for each of the electrode shanks 408, such that each of the electrode shanks 408 can be electrically coupled to an individual trace 402. In other implementations, the carrier substrate 418 includes fewer traces 420 than electrode shanks 408, such that multiple electrode shanks 408 can be electrically coupled to each trace 402.

Figure 9:
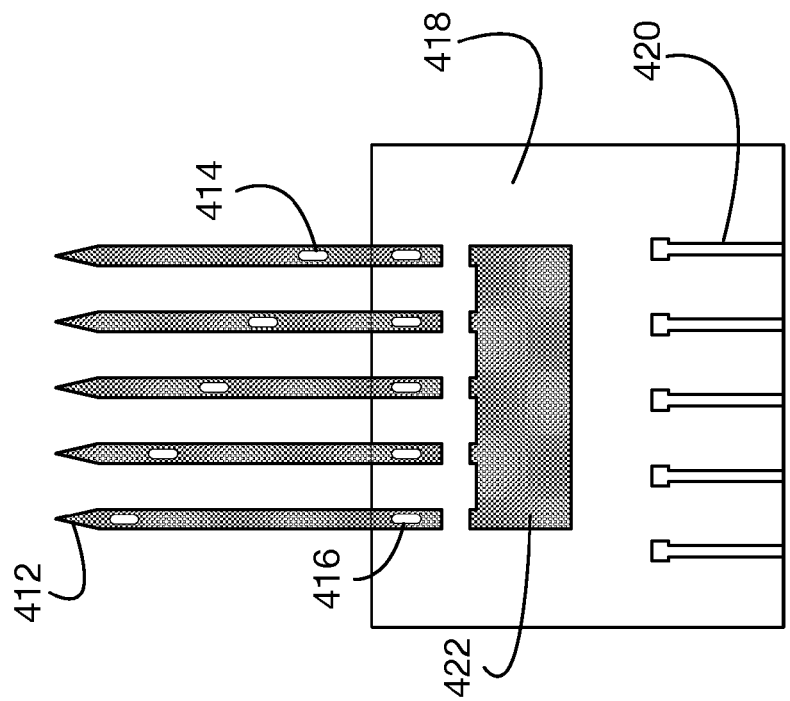

Referring to FIGS. 3 and 9, each of the electrode shanks are singulated (step 314). As illustrated in the above Figures, each of the electrode shanks 408 are coupled to one another through a common base 422. In some implementations, manufacturing each of electrode shanks 408 while each of the electrode shanks 408 are coupled to the common base 422 reduces manufacturing complexity because the common base 422 provides support and rigidity to the electrode shanks 408 during the placement of the electrode shanks 408 on the carrier substrate 418. Once coupled to the carrier substrate 418, the common base 422 is separated from each of the electrode shanks 408 to singulate the electrode shanks 408. The electrode shanks 408 can be singulated by laser ablating or micromachining a portion of each electrode shank 408 that connects to the common base 422. In some implementations, because the lower portions of each electrode shank 408 and the common base 422 are coupled to the carrier substrate 218 prior to singulation, the common base 422 remains coupled to the carrier substrate 418 after singulation. After the electrode shanks 408 are singulated, the contact pads 416 are electrically coupled to the traces 420 by, for example, wire bonding.

Figure 11:
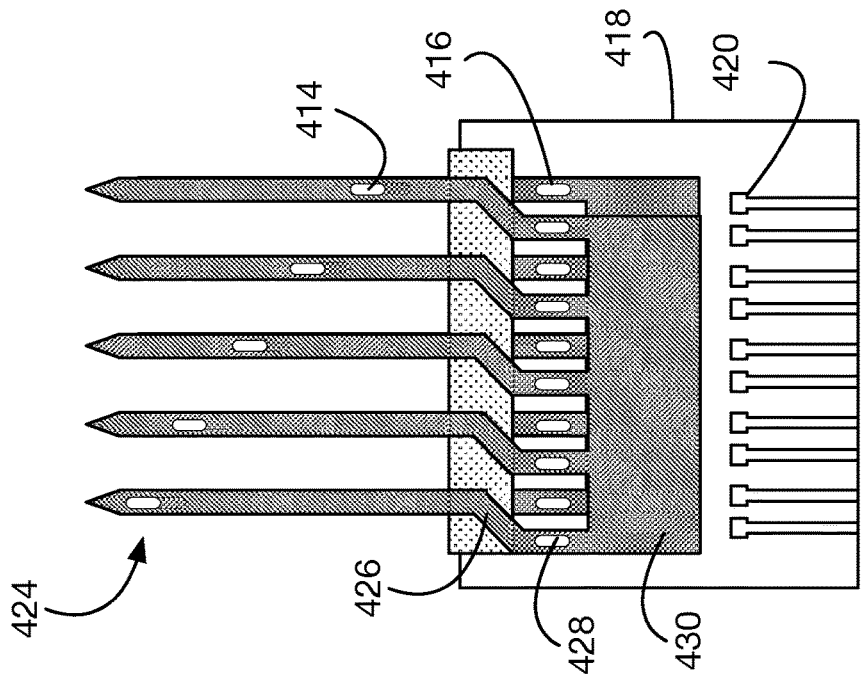
Figure 10:
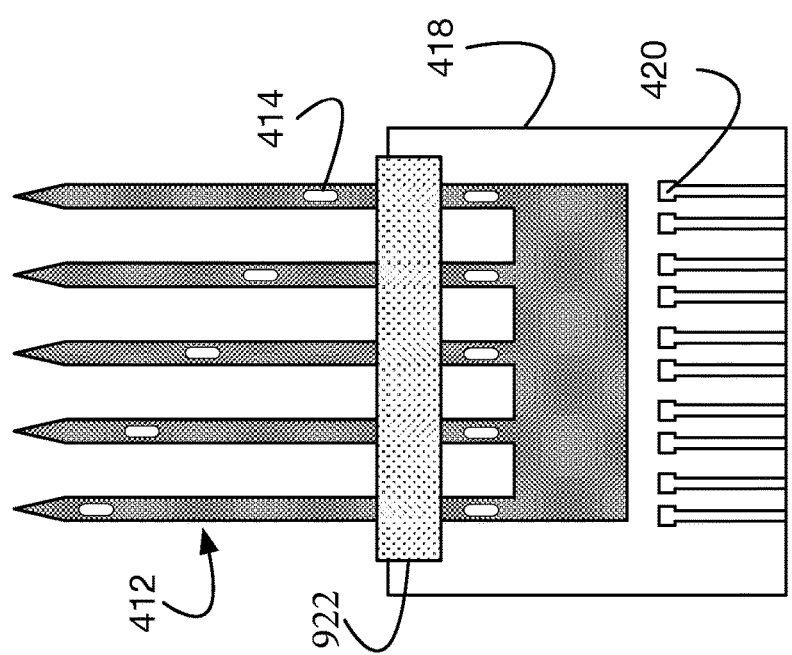
Figure 12:
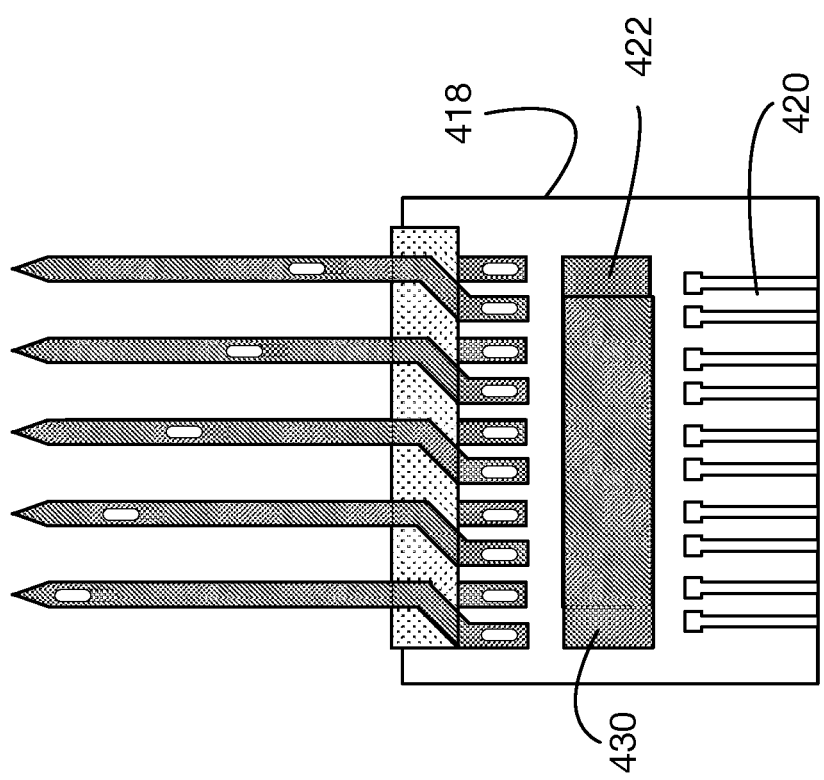

As described above, in some implementations, a three-dimensional electrode array is formed by stacking multiple rows of electrode shanks upon one another. FIGS. 10-12 illustrate an example method for stacking multiple rows of electrode shanks upon one another. FIG. 10 illustrates the encapsulated metal layer coupled to a carrier substrate 418 similar to as illustrated in FIG. 8. A spacing material 922 is coupled over the top of the electrode shanks 408. The spacing material 922 provides the spacing between the rows of electrode shanks 408. In some implementations, the spacing material 922 is between about 10 µm and about 500 µm, between about 10 µm and about 400 µm, between about 10 µm and about 300 µm, between about 10 µm and about 200 µm, between about 10 µm and about 100 µm, between about 10 µm and about 50 µm, or between about 10 µm and about 25 µm thick. The spacing material 922 includes a non-conductive material, such as the insulating material encapsulating each of the electrode shanks. As illustrated, the spacing material 922 is a separate component coupled to the base of the electrode shanks 408 and the carrier substrate 418. In other implementations, the spacing material 922 is a component of the encapsulated metal layer. For example, additional layers of the encapsulating material 412 can be patterned onto a portion of each of the electrode shanks 408 to provide spacing between each of the rows of electrode shanks.

FIG. 11 illustrates a top view of a second encapsulated metal layer coupled to a carrier substrate. A second encapsulated metal layer 424 is manufactured similar to the method described in relation to FIGS. 3A-7B. The electrode shanks of the second encapsulated metal layer 424 are aligned with the electrode shanks 408 of the first encapsulated metal layer. Each of the electrode shanks in the second encapsulated metal layer 424 includes an offset 426, which offset the contact pads 428 of the second encapsulated metal layer 424 from the contact pads 416 of the first encapsulated metal layer. Once the second encapsulated metal layer 424 is coupled to the spacing material 922, the portion of the second encapsulated metal layer 424 extending over the carrier substrate 418 (e.g., the common base 430 and portion of the electrode shanks near the contact pads 428) are bent toward and coupled to the carrier substrate 418.

FIG. 12 illustrates a top view the first and second encapsulated metal layers coupled to the carrier substrate. Once the encapsulating metal layers are coupled to the carrier substrate 418, the common base 422 and 430 are separated from each of the electrode shanks to singulate the electrode shanks. The electrode shanks can be singulated by laser ablating or micromachining a portion of each electrode shank that connects to the common base. After the electrode shanks are singulated, the contact pads 416 and 428 are electrically coupled to the traces 420 by, for example, wire bonding.

Figure 13A:
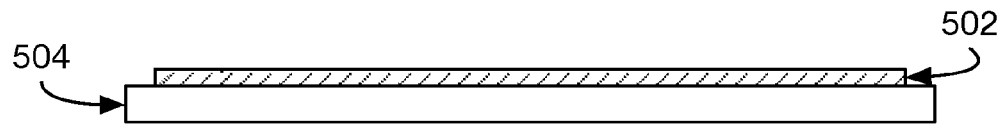
FIGS. 13A-13D illustrate another example method for patterning the metal layer in the method illustrated in FIG. 3.

Also referring to FIG. 3, FIGS. 13A-13D illustrate another example method for performing the step of patterning the metal layer (step 304) of method 300. FIG. 13A illustrates a cross-sectional view of a first stage of patterning a metal layer for step 304 of the method 300. A first metal layer 502 is deposited, by electroplating or sputtering, on a release layer 504. In some implementations, the first metal layer includes platinum, palladium, stainless steel, and platinum iridium.

Figure 13B:
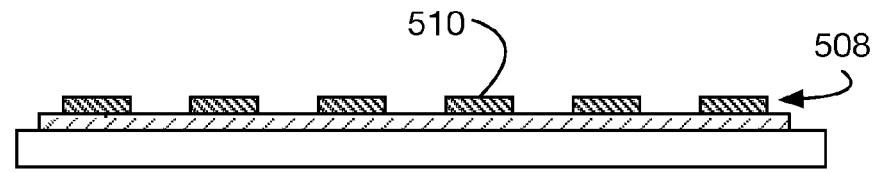

FIG. 13B illustrates a cross-sectional view of a second stage of patterning the metal layer for step 304 of the method 300. During the second stage, a second metal layer 508 is deposited onto the first metal layer 502. The second metal layer 508 includes a plurality of metal extrusions 510. In some implementations, the metal of the second metal layer 508 is copper. In some implementations, the copper core reduces the impedance of the electrode shank when compared to if the electrode shank was solid platinum.

Figure 13C:
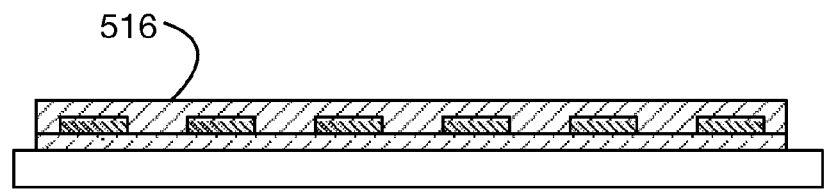

FIG. 13C illustrates a cross-sectional view of a third stage of patterning the metal layer for step 304 of the method 300. In the third stage, a third metal layer 516 is coupled to the second metal layer 508. For example, by sputtering or electroplating the third metal layer 516 atop the first metal layer 502 and the second metal layer 508. The third metal layer 516 encapsulates the extrusions 510 of the second metal layer 510. In some implementations, the third metal layer includes the same material of the first metal layer 502.

Figure 13D:
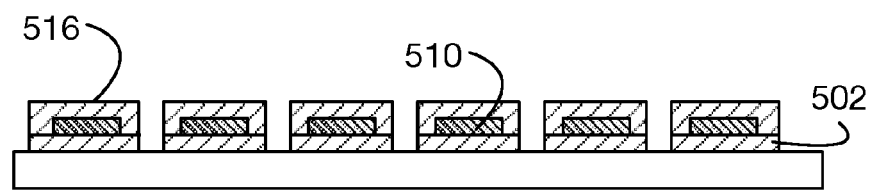

FIG. 13D illustrates a cross-sectional view of a fourth stage of patterning the metal layer for step 304 of the method 300. The first metal layer 502 and the third metal layer 516 are patterned for form the above described electrode shanks. In some implementations, the first metal layer 502 and the third metal layer 516 are patterned using laser ablation, or are chemical or plasma etched.

In some implementations, stacked, multiple rows of electrode shanks 520 are manufactured by repeating the stages illustrated in FIGS. 13A-13D. For example, to manufacture a second row of electrode shanks atop the electrode shanks 520 illustrated in FIG. 13D, a sacrificial layer is applied to the third metal layer 516. Then the steps illustrated in FIGS. 13A-13D are repeated to create a new row of electrode shanks atop the sacrificial layer deposited on the metal extrusions 518. Once the metal layer is patterned using the stages illustrated in FIGS. 13A-13D, the method 300 is continued at step 306.

Also referring to FIG. 3, FIGS. 14A-14G illustrate another example method for performing the step of forming the metal layer (step 304) of method 300. In some implementations, the metal layer is patterned through an additive manufacturing process such as the MICA Freeform process, made available by Microfabbrica Inc, headquartered in Van Nuys, Calif.

Figure 14A:
FIGS. 14A-14G illustrate another example method for patterning the metal layer in the method illustrated in FIG. 3.

FIG. 14A illustrates a cross-sectional view of a first stage of patterning the metal layer for step 304 of the method 300. A first metal layer 600 is deposited onto a sacrificial layer 602. In some implementations, the shape of the first metal layer is defined through photolithography. For example, the pattern of the first metal layer 600 is transferred onto a photoresist. The metal of the first metal layer 600 can then be electroplated onto into cavities formed within the photoresist. The photoresist can then be dissolved to leave the first metal layer 600.

Figure 14B:
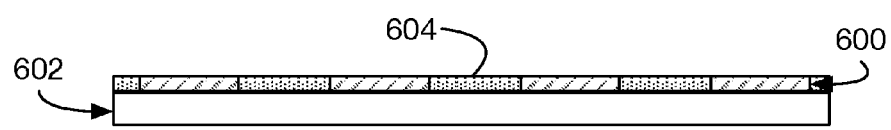

FIG. 14B illustrates a cross-sectional view of a second stage of patterning the metal layer for step 304 of the method 300. Once the photoresist has been dissolved, a sacrificial metal 604 is deposited over the first metal layer 600. In some implementations, the sacrificial metal 604 is copper. The sacrificial metal 604 is planarized down to the first metal layer 600 to expose the top of the first metal layer 600 and to create a flat surface for a second metal layer.

Figure 14C:
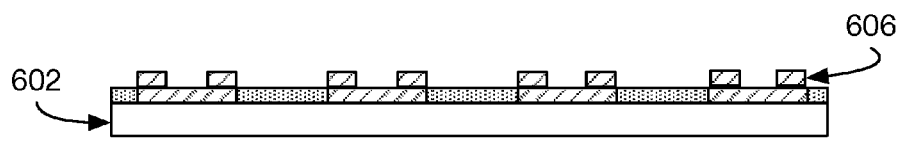

FIG. 14C illustrates a cross-sectional view of a third stage of patterning the metal layer for step 304 of the method 300. In a method similar to the method described in relation to FIG. 14A, a second metal layer 606 is deposited onto the first metal layer 600. In some implementations, the second metal layer 606 defines the side wall of the electrode shanks.

Figure 14D:
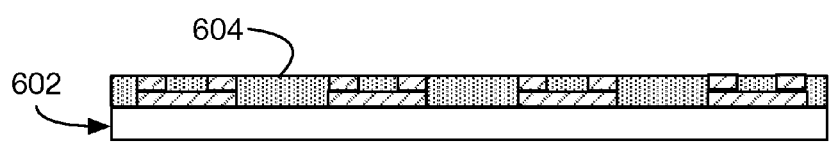

FIG. 14D illustrates a cross-sectional view of a fourth stage of patterning the metal layer for step 304 of the method 300. Another layer of the sacrificial metal 604 is deposited over the second metal layer 606. The sacrificial metal 604 is planarized down to the second metal layer 606 to expose the top of the first metal layer 606 and to create a flat surface for a third metal layer.

Figure 14E:
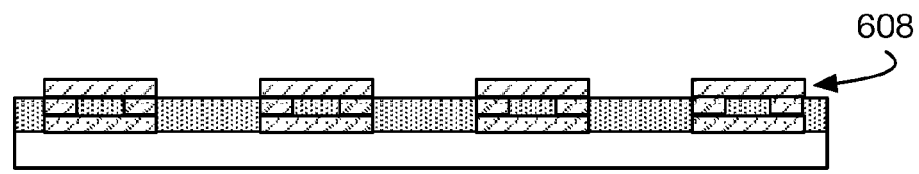

FIG. 14E illustrates a cross-sectional view of a fifth stage of patterning the metal layer for step 304 of the method 300. In a method similar to the method described in relation to FIG. 14A, a third metal layer 608 is deposited onto the second metal layer 606. In some implementations, the third metal layer 606 defines the top wall of the electrode shanks.

Figure 14F:
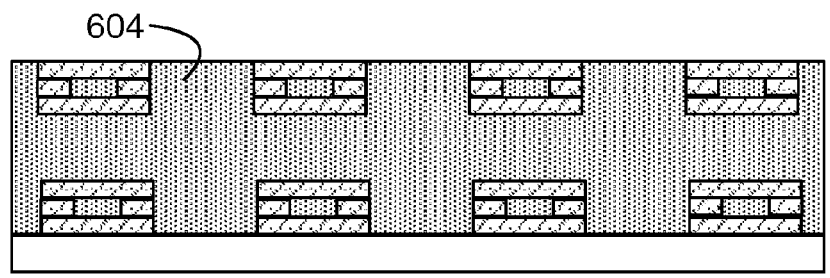

In some implementations, the stages described in relation to FIGS. 14A-14E are repeated to create multiple rows of electrode shanks. FIG. 14F illustrates a cross-sectional view of an electrode array with two rows of electrode shanks. In some implementations, to create spacing between the two rows of electrode shanks, multiple layers of the sacrificial metal 604 are deposited.

Figure 14G:
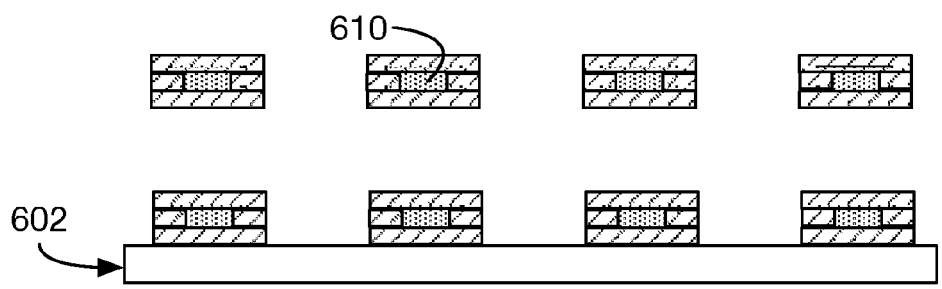

FIG. 14G illustrates a cross-sectional view of a final stage of patterning the metal layer for step 304 of the method 300. In the final stage, the sacrificial metal 604 is chemically etched away. A sacrificial metal core 610 (e.g., a copper core) remains within the center of each of the electrode shanks because the sacrificial metal core 610 core is fully encapsulated by the first, second, and third metal layers, which prevents the chemical etch from reaching the sacrificial metal core 610. In some implementations, the sacrificial metal core 610 reduces the impedance and resistance of the electrode shanks.

The disclosed system and methods may be embodied in other specific forms without departing from the spirit or essential characteristics thereof. The forgoing implementations are therefore to be considered in all respects illustrative, rather than limiting of the invention

What is claimed:

1. An electrode array comprising:
   a plurality of electrode shanks each comprising a central conductive core, and having a pitch between each of the plurality of electrode shanks of between about 10 μm and about 50 μm;
   an insulative layer encapsulating at least a portion of the central conductive core of each of the electrode shanks;
   an electrode on each of the plurality of electrode shanks, the electrode on each electrode shank defined by a first window through the insulative layer encapsulating the portion of the central conductive core of that electrode shank;
   a contact pad on each of the plurality of electrode shanks, the contact pad on each electrode shank defined by a second window through the insulative layer encapsulating the portion of the central conductive core of that electrode shank; and
   a carrier substrate, the plurality of electrode shanks coupled to a surface of the carrier substrate and extending outward from and parallel to the carrier substrate.

2. The electrode array of claim 1, further comprising a second plurality of electrode shanks coupled to the plurality of electrode shanks.

3. The electrode array of claim 2, wherein each of the second plurality of electrode shanks comprise an offset wherein a contact pad is defined in each of the second plurality of electrode shanks.

4. The electrode array of claim 1, wherein each of the plurality of electrode shanks are between about 5 μm and about 100 μm wide.

5. The electrode array of claim 1, wherein each of the plurality of electrode shanks are between about 5 μm and about 15 μm wide.

6. The electrode array of claim 1, wherein the plurality of electrode shanks comprises between about 2 and about 32 electrode shanks.

7. The electrode array of claim 1, wherein the electrode on each of the plurality of electrode shanks is located at a corresponding distance from a tip of that electrode shank, and wherein the corresponding distance for a first one of the electrodes is different from the corresponding distance for another one of the electrodes.

8. The electrode array of claim 1, wherein at least a portion of the carrier substrate is flexible.

9. The electrode array of claim 1, wherein the central conductive core comprises a platinum iridium foil.

10. The electrode array of claim 9, wherein the foil is between about 10 μm and about 40 μm thick.

11. The electrode array of claim 1, wherein the central conductive for of each of the plurality of electrode shanks is a copper core.

12. The electrode array of claim 1, further comprising a plurality of traces on the carrier substrate, wherein the contact pad of each of the plurality of electrode shanks is electrically coupled to one of the traces of the carrier substrate by wire bonding.

13. The electrode array of claim 1, wherein the contact pad on each electrode shank is disposed on a portion of that electrode shank that is in contact with the surface of the carrier substrate, and wherein the electrode on each electrode shank is disposed on a portion of that electrode shank that extends outward from and parallel to the carrier substrate.

14. The electrode array of claim 1, further comprising a metal layer on the carrier substrate, wherein the metal layer is:
- formed from a common material with the central conductive cores of the electrode shanks,
- coplanar with the central conductive cores of the electrode shanks, and
- electrically isolated from the electrode shanks.

15. The electrode array of claim 1, wherein each electrode shank includes a metal layer formed on the conductive core within the second window in the insulative layer encapsulating the portion of the central conductive core of that electrode shank.

* * * * *